(12) United States Patent
Lobato Salinas

(10) Patent No.: US 7,189,678 B2
(45) Date of Patent: Mar. 13, 2007

(54) METHOD FOR THE RECUPERATION OF DECAYED AGRICULTURAL PLANTATIONS

(76) Inventor: Antonio Danilo Lobato Salinas, Avenida 11 de Septiembre N° 1363, oficina 1404, Providencia, Santiago (CL)

( * ) Notice: Subject to any disclaimer, the term of this patent is extended or adjusted under 35 U.S.C. 154(b) by 187 days.

(21) Appl. No.: 10/378,877

(22) Filed: Mar. 5, 2003

(65) Prior Publication Data
US 2004/0033895 A1   Feb. 19, 2004

(30) Foreign Application Priority Data
Mar. 5, 2002   (CL) ........................................ 0428

(51) Int. Cl.
*A01N 43/16* (2006.01)
*A01G 17/02* (2006.01)
*C05D 3/00* (2006.01)

(52) U.S. Cl. ........................... 504/124; 504/292; 71/63

(58) Field of Classification Search ............... 504/124, 504/292; 71/63
See application file for complete search history.

(56) References Cited

U.S. PATENT DOCUMENTS

| | | | |
|---|---|---|---|
| 4,812,159 A | 3/1989 | Freepons | 71/16 |
| 4,886,541 A | 12/1989 | Hadwiger | 71/77 |
| 5,374,627 A | 12/1994 | Ito et al. | 514/55 |
| 5,720,793 A * | 2/1998 | Kato et al. | 71/16 |
| 5,733,851 A | 3/1998 | Villanueva et al. | 504/292 |

| | | |
|---|---|---|
| 2003/0024155 A1 | 2/2003 | Kuroda et al. |

FOREIGN PATENT DOCUMENTS

| | | |
|---|---|---|
| CA | 2 281 164 | 2/2001 |
| ES | 2 095 193 | 2/1997 |
| ES | 2 151 822 | 1/2001 |
| FR | 2 806 420 | 9/2001 |
| GB | 2 378 114 | 2/2003 |
| JP | 6-32704 * | 2/1994 |
| RU | 2 191 495 C1 | 10/2002 |
| RU | 2 193 590 | 11/2002 |

OTHER PUBLICATIONS

International Publication No. WO 02/074058 A1, published Sep. 26, 2002.
International Publication No. WO 02/063958 A1, published Aug. 22, 2002.
International Publication No. WO 03/016241 A1, published Feb. 27, 2003.
International Publication No. WO 02/064699 A2, published Aug. 22, 2002.
International Publication No. WO 02/38522 A2, published May 16, 2002.

* cited by examiner

*Primary Examiner*—S. Mark Clardy
(74) *Attorney, Agent, or Firm*—Arent Fox PLLC

(57) ABSTRACT

A method for the recovery of decayed agricultural plantations, preferably fruit orchards, or wine or table grape vineyards, where the plantation decay is due mainly to localized irrigation and the use of inadequate exploitation techniques, such as the traditional ones. The method consists in the use of non-localized irrigation in the plantation; the inclusion of $Ca^{++}$ providing substances in the soil; and the inclusion of a Chitosan solution (poly-D-glucosamine) in the irrigation water.

6 Claims, No Drawings

METHOD FOR THE RECUPERATION OF DECAYED AGRICULTURAL PLANTATIONS

CROSS-REFERENCE TO RELATED APPLICATIONS

This claims priority to Chilean patent application no. 0428, filed Mar. 5, 2002, the contents of which are incorporated herein in their entirety by reference.

BACKGROUND OF THE INVENTION

1. Field of the Invention

A method for the recuperation of decayed agricultural plantations is hereby presented, preferably for the case of fruit orchards, and wine and table grape vineyards, in which the decay of the plantation is mainly due to localized irrigation conditions and the use of inadequate exploitation techniques, such as traditional ones. The most significant consequence of decayed plantations is inadequate root development, and its consequent low level of productivity.

2. Description of the Related Art

Traditional plantation cultivation techniques, such as those that this invention covers, are based on the application of localized irrigation, whether it be drip emitters, irrigation tape, or micro sprinklers. Localized irrigation doesn't allow an adequate penetration of water to an appropriate depth in the soil when used according to traditional paradigms; it accumulates on the upper levels, and this leads to the sealing of the soil progressively closer to the surface, hampering the movement of water and the nutrients dissolved in it to deeper strata, and more importantly, affecting the oxygen levels in the soil. On the other hand, the excess of water in the soil profile at the depths where the irrigation bulb formed by drip irrigation generates an environment that is appropriate for the development of pathogens and which progressively concentrates salts in the soil, as these cannot be leached. The above-mentioned problems lead to a continued and progressive loss of agricultural aptitude of the soil in question.

The distribution of water at different depths in the soil affects, in addition to the above-mentioned, other chemical and mechanical aspects such as acidity, oxygenation, and porosity (or its opposite, compaction). The water that is found in, or that moves through the soil interstices, participates in the electrical dynamic of it and regulates the solid/liquid ionic exchange. Thus, the smallest presence of water favors the concentration of cations in the liquid phase, thereby favoring the accumulation of salts and toxic compounds such as aluminum ($Al^{+3}$) in the soil.

SUMMARY OF THE INVENTION

This invention offers a method for the recovery of physical, chemical, and biological characteristics of the soil, and to stimulate the recovery of root development in plants hampered by poor soil conditions. Basically, the invention is oriented towards the direct or indirect intervention in:

a) A more homogeneous distribution of irrigation water in the soil through the use of non-localized irrigation schemes;

b) An electrochemical and mechanical recovery of the soil through the use of substances that provide $Ca^{++}$ ions, with the subsequent improvement in soil aeration; and c) A stimulation of the plants defensive mechanisms, by including in the irrigation water a chitosan solution (poly-D-glucosamine) triggering synthesis processes in the plant that allow it to resist the attack of pathogens and increases root development. This aspect of the invention also favors the presence of an active micro fauna in the soil, as the use of chitosan solutions favors the survival of the chitinophagous fauna of the soil by maintaining an availability of a certain amount of chitin and chitosan around the plant, and this fauna is the natural enemy of many agricultural pests.

The effect of Chitosan on plants has been investigated by several researchers, and it's utilization in plants and seeds has been divulged, for example, in patents U.S. Pat. No. 4,812,159 of Freepons, U.S. Pat. No. 4,886,541 of Hadwiger, U.S. Pat. No. 5,374,627 of Ito et al. and U.S. Pat. No. 5,733,851 of Villanueva et al.

DETAILED DESCRIPTION OF THE INVENTION

The method of this invention includes basically the execution of three types of actions, not necessarily correlative, where these actions may be simultaneous or sequential.

One of the actions that participate in the method of this invention consists in providing the plant with non-localized irrigation, which uses the same volume of water as traditional plantations that use localized irrigation. This invention's irrigation method uses longer irrigation intervals than those used in traditional localized irrigation, thereby increasing the hydrostatic pressure on the soil surface, allowing water to reach deeper into the soil. This allows a more appropriate oxygenation and salt leaching, and an adequate distribution of nutrients dissolved and/or suspended in the water that reaches these deeper levels, allowing the plant to develop roots in areas where it previously could not.

For the determination of irrigation intervals, it is necessary to consider the plant species that will be subjected to the recovery process, considering the normal size of their roots for the productive age at which they are, and to compare it with the real size attained under decayed conditions. The irrigation interval determination is also dependant on how sealed the soil of the decayed plantation is, and the depth that the irrigation that was being used reached before the recovery of the plantation. These parameters may be defined more precisely by digging a trench between the rows of the plantation 0.70 to 0.90 m wide, and reaching a depth of 3.0 to 4.45 meters to inspect the true depth that the root mass and irrigation have reached, generally identifiable by the presence of a thin saline layer under which the soil is noticeably drier than above it.

The value of the irrigation intervals that turn out to be practical after analyzing the results of inspecting the trench will be called "appropriate irrigation intervals". It has been experimentally determined that a range of 3 to 18 hours of continuous irrigation is appropriate in most cases. The amount of water used in each irrigation, expressed as [mm water]/ha depends on the particular design of the equipment used, with variations of 1.0 to 1.55 mm/ha/hour. Regarding irrigation frequency, it will vary according to the species and phenological stages during the season, in ranges of 8 to 48 hours between irrigations.

The next action involved in this invention's method is the inclusion of substances that provide $Ca^{++}$ ions for the soil. Calcium Sulfate, Calcium Nitrate, and Calcium Carbonate are preferable, in proportion of 1 to 5 ton/ha. The substance that provides the $Ca^{++}$ may be applied dissolved in water or applied directly between the plantation rows, or in a combination of the above mentioned methods.

The last action in this invention's method—which allows the stimulation of the defensive response system of the plant—consists in the inclusion of a chitosan (poly-D-glucosamine) solution in the irrigation water, in proportions of between 0.001% and 0.075% by volume.

EXAMPLE 1

An example of the results obtained using this invention's method (Method for the Recovery of Decayed Agricultural Plantations, MRDAP):

An experiment was conducted during the 2000/2001 and 2001/2002 seasons, to demonstrate the effectiveness of this invention's method, on Red Globe table grapes, in a commercial plantation located in "El Palqui", IV Region, Chile, which showed noteworthy symptoms of decay.

The evaluated treatments, dosages used, and application dates are the following:

TABLE 1

"El Palqui" Treatments.

| Treatment | Root Flush (Nov. 11, 2000) | Root Flush (Mar. 17, 2001) | Root Flush (Nov. 1, 2001) |
|---|---|---|---|
| MRDAP | Chitosan solution 0.020% by weight/volume + Calcium sulfate (3 ton/ha) | Chitosan solution 0.020% by weight/volume | Chitosan solution 0.020% by weight/volume |
| Control | No application | No application | No application |

The results obtained were the following:

TABLE 2

Effect of MRDAP application on different production variables and on the development of plants, on Red Globe table grapes. "El Palqui", IV Region, 2001/2002 season.

| Treatments | Cluster Weight [kg] | Berry Weight [g] | Rakis weight [g] | Polar Diameter of Berries [mm] | Equatorial Diameter of Berries [mm] | Maturity [° Brix] | Trunk Diameter [cm] |
|---|---|---|---|---|---|---|---|
| MRDAP | 1.042 a | 11.91 a | 23.75 a | 27.9 a | 23.75 a | 15.6 a | 20.7 a |
| Control | 0.668 b | 8.83 b | 21.50 a | 25.7 a | 20.50 b | 16.3 a | 18.9 b |

Same letters show no statistical difference amongst each other. Duncan $p < 0.05$.

The results obtained indicate that there is a clear recovery effect due to the application of the method, considering the phenological activity of the plant, because not only did the measured productive variables (cluster weight, berry weight, and berry size) improve, but the plants also showed a greater general activity (trunk diameter and rachis weight) without affecting fruit maturity. On the other hand, given the textural characteristics of the locale, and the low salinity of the irrigation water, the calcium sulfate applications allowed an improvement of the water's infiltration speed in the soil profile, and a better aggregation of soil particles, which resulted in a better oxygenation of the roots.

The invention claimed is:

1. A method for the recovery of decayed agricultural plantations, comprising the following steps, not necessarily applied in the order described:
    a. Non-localized irrigation of the plantation for between 3 to 18 hours continuously, with a flow rate of between 1.00 to 1.55 mm/ha/hour, with non irrigation intervals of between 8 and 48 hours;
    b. inclusion of $Ca^{++}$ providing substances in a proportion of between 1 and 5 tons/ha; and
    c. inclusion of a chitosan solution in the irrigation water, in a proportion of between 0.001% and 0.075% by volume.

2. A method for the recovery of decayed agricultural plantations, such as mentioned in claim 1, where the substance that provides $Ca^{++}$ ions to the soil is mainly calcium sulfate.

3. A method for the recovery of decayed agricultural plantations, such as mentioned in claim 1, where the substance that provides $Ca^{++}$ ions to the soil is mainly calcium nitrate.

4. A method for the recovery of decayed agricultural plantations, such as mentioned in claim 1, where the substance that provides $Ca^{++}$ ions to the soil is mainly calcium carbonate.

5. A method for the recovery of decayed agricultural plantations, as in any one of claims 1 to 4, where the substances that provide $Ca^{++}$ ions are worked into the soil either alternately or in combination by applying them directly between the plantation rows, or dissolved in the irrigation water as described in step (1a.).

6. A method for the recovery of decayed agricultural plantations of claim 1, wherein the decayed agricultural plantations are selected from fruit orchards, wine vineyards, or table grape vineyards.

* * * * *